United States Patent [19]

Norton et al.

[11] 4,103,004

[45] Jul. 25, 1978

[54] CARDIOTONIC AGENT

[75] Inventors: Ted R. Norton; Midori Kashiwagi; Shoji Shibata, all of Honolulu, Hi.

[73] Assignee: University of Hawaii, Honolulu, Hi.

[21] Appl. No.: 828,712

[22] Filed: Aug. 29, 1977

[51] Int. Cl.² ...................... A61K 37/00; C07C 103/52
[52] U.S. Cl. ............................... 424/177; 260/112.5 R
[58] Field of Search .................. 260/112.5 R; 424/177

[56] References Cited

U.S. PATENT DOCUMENTS 3,951,939  4/1976  Fritz et al. ............................ 424/177

FOREIGN PATENT DOCUMENTS 1,411,184  1/1973  United Kingdom ................. 424/177

OTHER PUBLICATIONS

R. J. Quinn, et al., J. Pharm. Sci., 63, 1798–1800 (1974).
S. Shibata, et al., J. Pharm. Sci. 63, 1332 (1974).
G. Wunderer, et al., Hoppe–Seyler's Z. Physiol. Chem. 357, 239–240 (1976).
Beress, et al., Hoppe–Seyler's Z. Physiol. Chem. 357, 409–414 (1976).
L. Beress, et al., Toxicon 13, 359–367 (1975).
L. Beress, et al., Febs. Letter, 50, 311–314 (1975).

*Primary Examiner*—Delbert R. Phillips
*Attorney, Agent, or Firm*—Walter Patton; Harry E. Westlake, Jr.

[57] ABSTRACT

A novel peptide designated anthopleurin-C, hereinafter also referred to as AP-C, obtained from the sea anemone *Anthopleura elegantissima* is found to possess cardiotonic activity.

9 Claims, No Drawings

CARDIOTONIC AGENT

The invention described herein was made in the course of work under a grant from the United States Department of Health, Education and Welfare.

BACKGROUND OF THE INVENTION

The utility of the agents, currently used to stimulate the failing heart is limited by their toxic effects on the heart or by deleterious side effects on the peripheral circulation. For example, although the cardiac gylcosides are myocardial stimulants and can restore the failing heart, they do so at doses very close to those which produce toxic symptoms of cardiac arrhythmia, nausea and vomiting. The use of sympathomimetic agents are limited by associated arrhythmia, tachycardia, tachyphylaxis or altered peripheral resistance.

The compound of this invention primarily affects the contractile force of the heart muscle. The specific positive inotropic property of AP-C and the accompanying increase in cardiac output make it useful in the treatment of congestive cardiac failure or cardiac arrhythmias.

Anthopleurin-A (AP-A), a cardiotonic peptide obtained from *Anthopleura xanthogrammica*, has been described in U.S. Ser. No. 710,534, filed Aug. 2, 1976, and Norton et al., J. Pharmaceutical Sciences, Vol. 65, No. 9, 1368-1373, (1976). The present peptide differs substantially from AP-A with respect to the number, composition and sequence of amino acids. The peptide of the present invention is obtained from *Anthopleura elegantissima*. *Anthopleura elegantissima* is known to readily reproduce assexually in captivity thus providing an ample and reliable supply of AP-C. *Anthopleura xanthogrammica* is known not to reproduce in captivity thus the quantity of AP-Aavailable is limited to the amount of anemones which can be harvested from the ocean.

SUMMARY OF THE INVENTION

A novel peptide obtained from the sea anemone *Anthopleura elegantissima* has been discovered to have marked cardiac stimulant effects. Thus, it is the object of this invention to describe this novel peptide. It is a further object of this invention to describe the method of obtaining said novel peptide from sea anemone. A still further object is to describe compositions and the methods of treatment of heart failure or cardiac arrhythmias utilizing said peptide. Further objects will become apparent upon reading the following description and claims.

DESCRIPTION OF THE INVENTION

The novel peptide of the present invention, anthopleurin-C (AP-C), is obtained from the sea anemone *Anthopleura elegantissima* collected from the West Coast of California.

According to the present invention the live wet sea anemones are immersed in 95% ethanol and allowed to stand for about two weeks. During this period the AP-C is leached from the sea anemones into the preservative ethanol. The preservative ethanol is evaporated to leave a crude aqueous fraction. The crude aqueous fraction, containing anthopleurin-C, is subjected to gel filtration to give a twenty-fold increase in purity of anthopleurin-C. Alternatively, semi-permeable membranes may be used to accomplish the results obtained by gel filtration. Cation exchange chromatography provides an excellent separation of anthopleurin-C in a purity of about 25-30% depending on the particular collection of anemones. The balance is biologically inactive peptides and the buffer salts. To obtain analytically pure salt-free material the above material is further purified by gel filtration, twice by cation-exchange chromatography and by gel adsorption chromatography. All the separation procedures in the present invention are monitored by bioassay using the isolated rat atria for determination of positive inotropic effect using the procedure described in the section headed Bioassay.

According to a preferred process for obtaining anthopleurin-C, the collected live sea anemone *Anthopleura elegantissima* are placed in alcohol or an aqueous-alcoholic mixture and the AP-C allowed to leach out of the sea anemone into the alcohol. The leaching solution containing the AP-C is flash evaporated to remove the ethanol, extracted with chloroform, and is then subjected to gel filtration chromatography on a column packed with cross-linked dextran eluted with water, aqueous $NH_4HCO_3$ solution, or other volatile salt solution. The active fraction is lyophilized and chromatographed on a column packed with a cation-exchange resin and eluted with a buffer or with a buffer and a gradient of an ionizable salt solution. A suitable solution for eluting the cation-exchange resin is phosphate buffer or phosphate buffer with a gradient of NaCl solution. The active fraction is lyophilized to obtain the purified anthopleurin-C. The lyophilized material is about 0.5% anthopleurin-C, the balance being about 2% inactive polypeptides, buffer salts and sodium chloride. The active fraction is collected and desalted by chromatography on a column packed with cross-linked dextran resin eluted with a dilute solution of a low molecular weight organic acid, such as acetic acid.

To obtain analytically pure AP-C, the desalted material is subjected to ion exchange chromatography on a column packed with sulfoethyl cellulose eluted with pyridinium acetate buffers and gel adsorption chromatography on a column packed with cross-linked dextran eluted with 6% butanol in water and ammonium acetate buffer.

In a still further preferred process for obtaining anthopleurin-C from *Anthopleura elegantissima*, the live wet anemones are placed in 95% ethanol and kept at 0°-25° C. for 2 weeks. During this period, the AP-C is leached from the sea anemones into the preservative ethanol. The preservative alcohol is concentrated to an aqueous solution, which is centrifuged to remove solids and partitioned with chloroform. The chloroform extracted aqueous solution is lyophilized and the residue subjected to gel filtration chromatography on a column packed with cross-linked dextran such as Sephadex G-25, having an exclusion limit of 5,000 for globular proteins (manufactured by Pharmacia Fine Chemicals, Box 175, S-751 04, Uppsala 1, Sweden), and eluted with water. The fraction having Ve/Vo 1.15 to 1.7 contains anthopleurin-C purified seventeen-fold. The fraction Ve/Vo 1.15 to 1.7 is lyophilized and further purified by chromatography on a column packed with a weakly acidic cation exchange resin, such as CM-Sephadex C-25, eluted with a 0.03M, pH 6.5 phosphate buffer with gradient elution up to 0.3N NaCl. Anthopleurin-C elutes at Ve/Vo 5.4 to 6.9 and is lyophilized. The sodium chloride and phosphate salts are removed by placing a sample on a column packed with a cross-linked resin such as Sephadex G-10 having an exclusion limit of 700 followed by approximately three times sample volume of 20% sodium chloride solution and eluted with 0.017M acetic acid. Salt-free anthopleurin-C of 30 to 50% purity elutes at Ve/Vo 0.90 to 1.17. Since associated polypeptides were found to be inactive, this material is adequate for pharmacological studies.

To obtain AP-C free of associated inactive peptides, the Ve/Vo 0.90 to 1.17 fraction is dissolved in distilled water and chromatographed on Cellex-SE cellulose (Bio-Rad Laboratories, Richmond, California), equilibrated with 0.05M pyridine in 25% acetic acid. AP-C is eluted by a gradient of 0.05M pyridinium acetate pH 2.7 to 0.2M pyridine in 25% acetic acid, pH 3.1, in an area corresponding to about 0.1M pyridinium acetate.

This fraction is lyophilized and then dissolved in distilled water. The solution is charged to a column of Sephadex G-25, fine, and eluted with 6% n-butanol gradient with 0.05M $NH_4OAc$ (pH 6.0). The AP-C is eluted pure at about Ve/Vo = 3.0. This material now is analytically pure as judged by amino acid analysis and sequence determination.

The preferred process for obtaining pure anthopleurin-C is illustrated by the following Scheme 1.

Scheme 1
Extraction and Purification Scheme of
Anthopleurin-C from *A. elegantissima*

| | |
|---|---|
| 1.57 kg. | wet *A. elegantissima* in 6.62 l. 95% EtOH Flashed (<40° C.) to 1.5 l., extracted with 1.7 l. $CHCl_3$, centrifuged and lyophilized |
| 88.6 g. | $H_2O$ soluble An 11.1 g. portion of $H_2O$ soluble was subjected to gel filtration chromatography on 2500 ml. Sephadex G-25 |
| 0.634 g. Ve/Vo = | Fraction A, active 1.12 – 1.67 |
| | CM-Sephadex C-25 eluted with phosphate buffer at pH 6.5 and gradient elution with 0.3N NaCl |
| 1.04 g. Ve/Vo = | Fraction B (including salts) 5.4 – 6.9 Desalted on Sephadex G-10 eluted with 0.017M acetic acid |
| 21.7 mg. Ve/Vo = | 20 to 50% pure AP-C, Fraction C 0.90 – 1.17 |
| 43.4 mg. | Fraction C Gradient elution on SE-cellulose with 0.05M pyridine to 0.2M pyridine both in 25% acetic acid |
| 16.2 mg. Ve/Vo = | Approximately 80% pure AP-C, Fraction D 2.8 – 3.5 |
| | Repeat |
| 12.9 mg. | Approximately 90% pure AP-C, Fraction E |
| 25.7 mg. | Fraction E Gradient elution on Sephadex G-25 with 6% n-butanol to 0.05M $NH_4OAc$ |
| 22.4 mg. Ve/Vo = | 98% pure AP-C, Fraction F 2.12 – 2.74 (28.5 ppm based on starting anemones wet wt.) |

The novel peptide, AP-C, of the present invention is administered to the patient with heart failure or cardiac arrhythmias at a rate of from about 0.01 to about 5 μg/kg. of body weight per hour either by infusion or by a single dose as determined by those skilled in the art.

For such usage the compound of this invention may be administered orally or parenterally as such or admixed with conventional pharmaceutical carriers. The parenteral route is preferred. It may be administered orally in such forms as tablets, dispersible powders, granules, capsules, syrups and elixirs, and parenterally as solutions, suspensions, dispersions, emulsions, and the like, e.g., a sterile injectable aqueous solution. The compound may also be altered chemically such as by acylation and esterification, or physically such as preparing an artificial liposome to reduce peptic destruction. The preferred route of administration is by injection.

A preferred pharmaceutical composition of AP-C comprises the active ingredient in gelatin and phenol preservative. A further preferred pharmaceutical composition for injection comprises sterile powdered lyophilized AP-C which in the dry form is stable at room temperature. The lyophilized powder may be packaged in vials containing hydrolyzed gelatin. AP-C may be reconstituted at the time of use by dissolving in a convenient volume of sterile water or sodium chloride solution for injection in such a manner that the individual dose will be contained in 1–2 ml. of solution. The reconstituted solution should be refrigerated and used before decomposition or preferably within 24 hours.

These pharmaceutical preparations may contain up to about 90% of the active ingredient in combination with the carrier or adjuvant.

The cardiotonic effective dosage of active ingredient employed for the treatment of congestive heart failure or cardiac arrhythmias may vary depending on the severity of the condition being treated. However, in general, satisfactory results are obtained when anthopleurin-C is administered at an hourly dosage of from about 0.01 μg to about 5 μg/kg of animal body weight, or in sustained release form for the period of time which is determined by those skilled in the art.

Dosage forms suitable for internal use comprise from about 2 to about 360 μg of the active compound in intimate admixture with a solid or liquid pharmaceutically acceptable carrier or diluent. The preferred pharmaceutical compositions from the standpoint of preparation and ease of administration are injectable compositions, particularly those containing about 0.05 μg to about 10 μg/ml.

Bioassay for Determining Positive Inotropic Effect

Bioassays of the solutions containing anthopleurin-C are performed on isolated atria of rat hearts. The atrium is separated from the rest of the heart and suspended in an isolated organ bath (20, 25, or 50 ml.) containing Krebs Ringer bicarbonate medium (pH 7.4) of the following composition in distilled deionized water (in mmoles): $Na^+$, 145; $K^+$, 6.02; $Ca^{+2}$, 1.22; $Mg^{+2}$, 1.33; $Cl^-$, 126; $HCO_3^-$, 25.3; $PO_4^{-3}$, 1.2; $SO_4^{-2}$, 1.33; and glucose, 5.5. The temperature of the organ bath is maintained at 30° C., and the Krebs-Ringer medium is continuously aerated with 95% $O_2$—5% $CO_2$.

The spontaneously beating atrial preparation is connected by a thin silk thread to a force-displacement transducer (Grass model FT.03), and the contractile movements are recorded on a six-channel polygraph Grass Model 7. The preparation is allowed to equilibrate under 750 mg. tension for 60 minutes prior to beginning an assay. After this equilibration, during which the preparations are washed out every 30 minutes, the spontaneous beat rate of the atria remains constant; the change during a 10-minute observation being less than 5 beats/min. The changes in contractile force and rate produced by the test solution containing anthopleurin-C is expressed as a percentage increase or decrease in tension and rhythm, with the period immediately preceding addition of test solution to the tissue bath as the baseline for comparison.

PHYSICAL AND CHEMICAL PROPERTIES OF AP-C

For the purpose of obtaining electrophoretic properties, the anthopleurin-C obtained in Example 1, Steps a through d below, was rechromatographed on CM Sephadex C-25, and G-10 according to the process set forth in Example 1, Steps c, and d, respectively. The doubly purified material was subjected to electrophoretic analysis using commercially available pre-cast 12% acrylamide gels and matched buffer systems obtained from Bio-Rad Laboratories, 32nd and Griffin, Richmond, California.

Isoelectric focusing gave the isoelectric point at a pH = 8.0. Disc gel electrophoresis with 12% polyacrylamide gel at pH 3.6 gave an $R_f$ value of 0.49 versus methyl green tracking dye. AP-C does not enter a basic gel at pH 8.9 indicating possible lack of available carboxyls. Sodium dodecyl sulfate (SDS) disc gel electrophoresis using a 10% gel indicated a m.w. of about 5,200 after incubation with dithioerythritol, using RNase A and pancreatic trypsin inhibitor (PTI) for comparison. The molecular weight is so low that these values are only approximate. AP-C was determined to be a peptide on the basis of loss of biological activity after treatment with proteolytic enzymes.

Amino acid sequencing of the analytically pure S-carboxymethylated anthopleurin-C gave the following sequence (in agreement with the amino acid analysis of a hydrolysate): Gly-Val-Pro-Cys-Leu-Cys-Asp-Ser-Asp-Gly-Pro-Ser-Val-Arg-Gly-Asn-Thr-Leu-Ser-Gly-Ile-Leu-Trp-Leu-Ala-Gly-Cys-Pro-Ser-Gly-Trp-His-Asn-Cys-Lys-Ala-His-Gly-Pro-Thr-Ile-Gly-Trp-Cys-Cys-Lys-Gln.

This sequence corresponds to a molecular weight of 4,875 daltons.

The abbreviated designations, which are used herein for the amino acid components are as follows:

| Abbreviated Designation | Amino Acid |
| --- | --- |
| Lys | lysine |
| His | histidine |
| Arg | arginine |
| Asp | aspartic acid |
| Thr | threonine |
| Ser | serine |
| Gln | glutamine |
| Pro | proline |
| Gly | glycine |
| Ala | alanine |
| Cys | cysteine |
| Val | valine |
| Ile | isoleucine |
| Leu | leucine |
| Trp | tryptophan |
| Asn | asparagine |

Anthopleurin-C is relatively stable at neutral and lower pH values and is very soluble in deionized water.

Anthopleurin-C can be further characterized by its pharmacological characteristics. The pharmacological characteristics indicate anthopleurin-C is about 200–1000x as potent as ouabain in positive inotropic effect, having an $ED_{50}$ at $3.0 \times 10^{-9}$M on isolated rat atria. It does not show any chronotropic effect.

EXAMPLE 1

Isolation of Anthopleurin-C from Anthopleura elegantissima

Step a — Leaching

*Anthopleura elegantissima* (Brandt) specimens (1.57 kg.) were collected, preserved in 95% ethanol (1 kg. anemones/3.785 l. 95% EtOH) and stored at 4° C. The preservative ethanol was filtered through cheesecloth and the filtrate was flash evaporated at ≦ 40° C. to about 1.5 liters and partitioned with an equal volume of chloroform bathwise, by thorough agitation followed by centrifugation at 27,000 × g. for 30 minutes. This produced 88.6 g (lyophilized weight) of water solubles containing anthopleurin-C.

Step b — Gel Permeation Chromatography 88.6 g of crude water soluble extract, containing anthropleurin-C, was split into eight equal portions for chromatographic separation on Sephadex G-25 having an exclusion limit 5,000 (obtained from Pharmacia Fine Chemicals). A 53 × 8.3 cm. column containing 2,500 ml. of wet Sephadex G-25 (Vo = 1000 ml.) was equilibrated with water saturated with chloroform (to prevent micro-organism growth). Fifty ml. of water containing 11.1 g. of crude water soluble extract containing anthopleurin-C was placed on the column and eluted with $H_2O$ at 8–9 ml./min. at room temperature. The active fraction (A) eluting at Ve/Vo 1.12 - 1.67 was collected and lyophilized. It weighed 0.634 g.

Step c — Ion-exchange Chromatography

A 634 mg. portion of fraction A, obtained in Step b, was dissolved in 5 ml. of 0.03M sodium phosphate buffer at pH 6.5 and put on a 48 × 4 cm. column (Vo = 185 ml.) containing 550 ml. of wet cation exchange resin CM-Sephadex C-25 (obtained from Pharmacia Fine Chemicals) equilibrated with the same buffer saturated with chloroform. A stirred reservoir of 1,000 ml. of the buffer was connected to the column and the reservoir volume was maintained constant by feeding with a 0.03M sodium phosphate buffer 0.3M in NaCl adjusted to pH 6.5 for gradient elution. Both solutions were saturated with chloroform. The flow rate of about 3 ml./min. was maintained and the run was made at room temperature. The effluent was monitored using U.V. absorbance at 280 nm with a Model UA-5 Absorbance Monitor, obtained from Instrument Specialties Company, P.O. Box 5247, 4700 Superior Street, Lincoln, Nebraska 68505. The fraction having the Ve/Vo range between 5.4 and 6.9 and centered at Ve/Vo 6.0 was designated fraction B and found to be active according to the bioassay set forth under the heading Bioassay. Fraction B was lyophilized to give 1.04 g. of material, containing anthopleurin-C admixed with salts.

Step d — Desalting

The salts were removed by using a column packed with Sephadex G-10 having an exclusion limit of 700 (obtained from Pharmacia Fine Chemicals). The 1.04 g. of fraction B, obtained in Step c, was dissolved in 10 ml. of $H_2O$ and put on a 3.0 × 31 cm. column packed with 230 ml. wet Sephadex G-10 equilibrated with 0.017M acetic acid saturated with chloroform. The sample was followed by 5.0 ml. of 20% NaCl and then the equilibrating solution. Anthopleurin-C emerged completely and sharply at void volume (Ve/Vo 0.90 - 1.17) and was salt free. It was immediately lyophilized to give 21.7 mg. of 20—50% pure anthopleurin-C.

Step e — Gradient Elution on SE Cellulose

The peptide (43.4 mg.) obtained by the process set forth in Steps a) to d), was dissolved in 1 ml. of distilled water and placed on a 2.1 × 39 cm. column packed with 135 ml. wet Cellex-SE cellulose (Bio-Rad Laboratories, Richmond, California), equilibrated with 0.05M pyridine in 25% acetic acid. Using a 250 ml. stirred reservoir of the 0.05M pyridine, a gradient with 0.20M pyridine in 25% acetic acid was produced by allowing the latter to flow into the former as it was used in elution. The active peptide was eluted at Ve/Vo 2.8 —3.5 and after lyophilization weighed 16.2 mg. This procedure was repeated to remove the last of an impurity at Ve/Vo = 2.54; the active peptide fraction E then weighed 12.9 mg.

Step f — Gradient Elution on Sephadex G-25

A 25.7 mg. sample of peptide produced as in Step e) was dissolved in 0.5 ml. distilled water and placed on a 1.1 × 58 cm. column packed with 55 ml. Sephadex G-25, fine, equilibrated with 6% n-butanol in distilled water. Using a 500 ml. stirred reservoir of the 6% butanol a gradient with 0.05M $NH_4OAc$ in 6% butanol was produced by allowing the latter to flow into the former as it was used for elution. The active peptide was eluted at Ve/Vo 2.12 — 2.74 and after lyophilization gave 22.4 mg. of 98% pure anthopleurin-C.

EXAMPLE 2

Sterile Suspension of AP-C for Injection

The anthopleurin-C obtained in Example 1 is mixed with sterile hydrolyzed gelatin to the extent of 3.5 μg anthopleurin-C to about 10 mg. hydrolyzed gelatin and packaged in sterile vials sealed in an atmosphere of nitrogen using conventional techniques. The AP-C is reconstituted at the time of use by the addition of 1 ml. sterile water. The injectable solution is suitable for administration once an hour for a body weight of 70 kg.

What is claimed is:

1. A peptide designated anthopleurin-C having the amino acid sequence:

Gly-Val-Pro-Cys-Leu-Cys-Asp-Ser-Asp-Gly-Pro-Ser-Val-Arg-Gly-Asn-Thr-Leu-Ser-Gly-Ile-Leu-Trp-Leu-Ala-Gly-Cys-Pro-Ser-Gly-Trp-His-Asn-Cys-Lys-Ala-His-Gly-Pro-Thr-Ile-Gly-Trp-Cys-Cys-Lys-Gln.

2. A process for the preparation of anthopleurin-C from sea anemone, which comprises:
    (a) leaching the sea anemones with water or with an aqueous-alcoholic mixture;
    (b) subjecting the concentrated aqueous solution from evaporation of the leaching solvent to gel filtration chromatography on a column of cross-linked dextran eluted with water and collecting and lyophilizing the active fraction; P1 (c) subjecting the active fraction to chromatography on a column of cation exchange resin eluted with a phosphate buffer with a gradient of NaCl and collecting and lyophilizing the active fraction.

3. A process according to claim 2, which comprises:
    (d) desalting the active fraction obtained in (c) by chromatography on a column of cross-linked dextran eluted with dilute acetic acid and collecting and lyophilizing the active fraction.

4. The process according to claim 2, wherein the sea anemone is *Anthopleura elegantissima*.

5. The process according to claim 4 which comprises the following steps:
    (a) leaching the sea anemone, *Anthopleura elegantissima*, with 95% aqueous ethanol;
    (b) subjecting the concentrated leaching solution to gel filtration chromatography on a column of cross-linked dextran having an exclusion limit of 5,000 eluted with water and collecting and lyophilizing the active fraction;
    (c) subjecting the active fraction to chromatography on a column of weakly acidic cation exchange resin eluted with 0.03M phosphate buffer at pH 6.5 and a gradient of 0.3N NaCl, collecting and lyophilizing the active fraction.

6. The process according to claim 5 which comprises:
    (d) desalting the active fraction obtained in (c) by placing a solution of said active fraction on a column of cross-linked dextran with an exclusion limit of 700 followed by a solution of 20% sodium chloride solution and eluting with 0.017M acetic acid and collecting and lyophilizing the active fraction,
    (e) subjecting the active fraction obtained in (d) to gradient elution on sulfoethyl cellulose wherein the gradient is from 0.05M pyridine to 0.2M pyridine in 25% acetic acid and collecting and lyophilizing the active fraction,
    (f) subjecting the active fraction obtained in (e) to gradient elution on a column of cross-linked dextran wherein the gradient is from 6% n-butanol to 0.05M $NH_4OAc$ in 6% n-butanol.

7. The pharmaceutical preparation which comprises the peptide of claim 1 in admixture or conjunction with a pharmaceutically acceptable carrier.

8. The method of treating heart failure by administering a cardio effective amount of the peptide of claim 1.

9. The method of treating cardiac arrhythmias by administering a cardio effective amount of the peptide of claim 1.

* * * * *